United States Patent
Alaofi

(10) Patent No.: US 12,202,868 B1
(45) Date of Patent: Jan. 21, 2025

(54) STAPLED AND SPECIFICALLY TARGETED ANTIMICROBIAL PEPTIDE

(71) Applicant: KING SAUD UNIVERSITY, Riyadh (SA)

(72) Inventor: Ahmed Lafi Alaofi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/666,750

(22) Filed: May 16, 2024

(51) Int. Cl.
*C07K 14/47* (2006.01)
*A61K 38/00* (2006.01)

(52) U.S. Cl.
CPC .......... *C07K 14/4723* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,957,026 B2 | 2/2015 | Verdine | |
| 10,464,975 B2 | 11/2019 | Walensky | |
| 11,325,955 B2 | 5/2022 | Walensky | |
| 2005/0250680 A1 | 11/2005 | Walensky | |
| 2006/0287232 A1 | 12/2006 | Clayberger | |

FOREIGN PATENT DOCUMENTS

| | | |
|---|---|---|
| CN | 1597695 A | 3/2005 |
| KR | 102521182 B1 | 4/2023 |
| WO | 2022/236009 A2 | 11/2022 |

OTHER PUBLICATIONS

Hersh et al. (Clinical Infectious Diseases 2012;54(11):1677-8) (Year: 2012).*
Medical News Today (downloaded from URL:<https://www.medicalnewstoday.com/articles/staph-infection-vs-mrsa#Causes>) (Year: 2024).*
Costello et al. (Pancreat Disord Ther; Suppl 4; doi:10.4172/2165-7092.S4-002, 2013) (Year: 2013).*
Mourtada, R., et al., "Design of Stapled Antimicrobial Peptides that Overcome Antibiotic Resistance and In Vivo Toxicity", Nat. Biotechnol. 37(10): 1186-1197 (2019).

* cited by examiner

*Primary Examiner* — Sergio Coffa
(74) *Attorney, Agent, or Firm* — Nath, Goldberg & Meyer; Joshua B. Goldberg

(57) ABSTRACT

A stapled and specifically targeted antimicrobial peptide having the amino acid sequence LPSTGEKD-TAVERNGGFFRKSKEK-S5-GKE-S5-KRIV (SEQ ID NO: 1) and its use as an antimicrobial and anticancer agent are provided.

8 Claims, 2 Drawing Sheets
Specification includes a Sequence Listing.

SEQUENCE LISTING

```
Sequence total quantity: 4
SEQ ID NO: 1              moltype = AA  length = 33
FEATURE                   Location/Qualifiers
source                    1..33
                          mol_type = protein
                          organism = synthetic construct
MOD_RES                   9
                          note = alpha-4-n-pentenylalanine
MOD_RES                   13
                          note = alpha-4-n-pentenylalanine
BINDING                   9..13
                          note = hydrocarbon staple
SEQUENCE: 1
LPSTGEKDTA VFRNGGFFRK SKEKXGKEXK RIV                                33

SEQ ID NO: 2              moltype = AA  length = 17
FEATURE                   Location/Qualifiers
source                    1..17
                          mol_type = protein
                          organism = synthetic construct
SEQUENCE: 2
FFRKSKEKXG KEXKRIV                                                  17

SEQ ID NO: 3              moltype = AA  length = 14
FEATURE                   Location/Qualifiers
source                    1..14
                          mol_type = protein
                          organism = synthetic construct
SEQUENCE: 3
LPSTGEKDTA VFRN                                                     14

SEQ ID NO: 4              moltype = AA  length = 17
FEATURE                   Location/Qualifiers
source                    1..17
                          mol_type = protein
                          organism = synthetic construct
SEQUENCE: 4
FFRKSKEKSG KESKRIV                                                  17
```

STAPLED AND SPECIFICALLY TARGETED ANTIMICROBIAL PEPTIDE

SEQUENCE LISTING

The instant application contains a Sequence Listing which has been submitted in XML format via Patent Center and is hereby incorporated by reference in its entirety. Said XML copy, created on Mar. 30, 2024, is named 3309265U.xml and is 6000 bytes in size.

BACKGROUND

1. Field

The present disclosure relates generally to a stapled antimicrobial peptide (ssTAMP2), and particularly to a stapled and specifically targeted antimicrobial peptide (ssTAMP2) that can be used as a microbial inhibitor.

2. Description of the Related Art

The uprising of antimicrobial resistance is an alarming threat that might cause a future pandemic globally. The World Health Organization (WHO) has declared antimicrobial resistance as one of the top 10 global public health threats. Multi-drug resistant (MDR) pathogens are the most frequently reported causes of antimicrobial resistance. For example, methicillin-resistant *Staphylococcus aureus* (MRSA) and multidrug-resistant Gram-negative bacteria are responsible for a high percentage of hospital-acquired infections.

It has been recognized that antimicrobial peptides (AMPs) can potentially be effective agents against multi-drug resistant bacteria. There are 2800 AMPs discovered so far, but few of the AMPs are in use therapeutically (such as daptomycin and melittin). Around 50 AMPs are still in preclinical and clinical trials. Moreover, some AMPs in clinical trials have certain limitations, such as instability in biological fluids, unfavorable pharmacokinetics profiles, hemolytic effects, similar activities to traditional antibiotics (Phase III), and other adverse effects. For instance, Friulimicin B was studied in several murine infection models but showed different responses in *Bacillus subtilis* when compared to daptomycin, due to differences in pharmacokinetic profiles.

Therefore, implementing specifically targeted antimicrobial peptides (STAMPs) that combat antimicrobial resistance, with no or less effect on the normal commensals, is desired. STAMPs are typically composed of two or more functional regions; one for specific targeting and the other for killing the targeted microbe, with both regions being functionally independent and linked by a linker.

The proposed mechanism of STAMPs suggests that targeting moieties first initiate binding, thus allowing accumulation of killing moieties in a particular pathogen (Sarma et al., 2018; León-Buitimea et al., 2020; Xu et al., 2020). Other ways to overcome limitations of using AMPs is by implementing a staple strategy for antimicrobial peptides. Simply, the stapling strategy relies on fixing α-helix structures of AMPs, thereby, overcoming the limitation of using AMPs. This is because most AMPs have an α-helix structure and this secondary structure plays an important role in AMP activity and specificity (Mourtada et al., 2019; Madanchi et al., 2020).

The binding interactions of known AMPs to their target have been studied. Due to AMP characteristics, i.e., positively charged molecules with hydrophilic and hydrophobic regions, the electrostatic interactions between AMPs and the target's cell membrane (negatively charged) can initiate binding. This AMP interaction can be based on cell wall composition. For instance, lipopolysaccharide (LPS)-binding peptides show an ability to neutralize LPS and kill Gram-negative pathogens. One example is cathelicidins peptides (rabbit and human) that can bind to LPS.

H. Madanchi et al. investigated CAP18 peptides (derived from cationic antibacterial protein 18 KDa) in in-silico and in-vitro studies that showed truncated derivatives from CAP18 peptide to improve antibacterial activity and LPS-binding properties. It is worth mentioning, a Trp reside substituent increases one of the CAP18 derivative binding to LPS that indicates the role of hydrophobicity in the binding interaction.

Another LPS-binding peptide is LL-37 peptide, one of the principal human AMPs, that possesses antimicrobial activity. LL-37 shows activity against Gram-negative and Gram-positive bacteria. Studies showed that peptides from LL-37 that include a core antimicrobial region have better antimicrobial activity. D. Berif et al. showed synthetic LL-37 derivatives to enhance antibacterial and antibiofilm activities.

Bacterial infection remains a significant threat to human life due to its increasing resistance to conventional antibiotics, which is a growing public health concern. One effective strategy for dealing with multidrug resistance among harmful bacteria is the production of alternative new antibacterial drugs. The remarkable antibacterial effects of specifically targeted antimicrobial peptides (STAMPs) have been well documented. However, STAMPs have yet to be developed into safe and effective treatments.

Accordingly, there remains a need for new and effective specifically targeted antimicrobial peptides (STAMPs) which are designed to selectively target and kill a specific pathogen. Thus, new specifically targeted antimicrobial peptides as antimicrobial agents solving the aforementioned problems are desired.

SUMMARY

The present subject matter pertains to a stapled and specifically targeted antimicrobial peptide (ssTAMP2) including a functional group, a linker, and a targeting group, and its use as an antimicrobial agent.

In an embodiment, the present subject matter relates to a stapled and specifically targeted antimicrobial peptide (ssTAMP2) having the sequence LPSTGEKD-TAVERNGGFFRKSKEK-S5-GKE-S5-KRIV-NH2 (SEQ ID NO: 1). In an embodiment, the ssTAMP2 peptide includes alpha-4-n-pentenyl alanine (S5) residues (non-naturally occurring amino acid residues). In an embodiment, the present subject matter relates to a pharmaceutical composition comprising the ssTAMP2 peptide and a pharmaceutically acceptable carrier.

In an embodiment, the present subject matter relates to a process for the synthesis of the ssTAMP2 peptide, including providing a cathelicidin antimicrobial peptide having the sequence FFRKSKEKIGKEFKRIV (SEQ ID NO: 4), and replacing the isoleucine at position 9 of SEQ ID NO: 4 and the phenylalanine residue at position 13 of SEQ ID NO: 2 with alpha-4-n-pentenylalanine residues (S5).

Further contemplated herein are pharmaceutical compositions comprising the stapled and specifically targeted antimicrobial peptide (ssTAMP2) of SEQ ID NO: 1, as well as methods for inhibiting microbial growth or treating or ameliorating microbial infections or inhibiting cancer cell growth by administering the stapled and specifically targeted antimicrobial peptide (ssTAMP2) of SEQ ID NO: 1 to a patient in need thereof.

These and other features of the present subject matter will become readily apparent upon further review of the following specification.

DETAILED DESCRIPTION OF THE PREFERRED EMBODIMENTS

Figure 1:
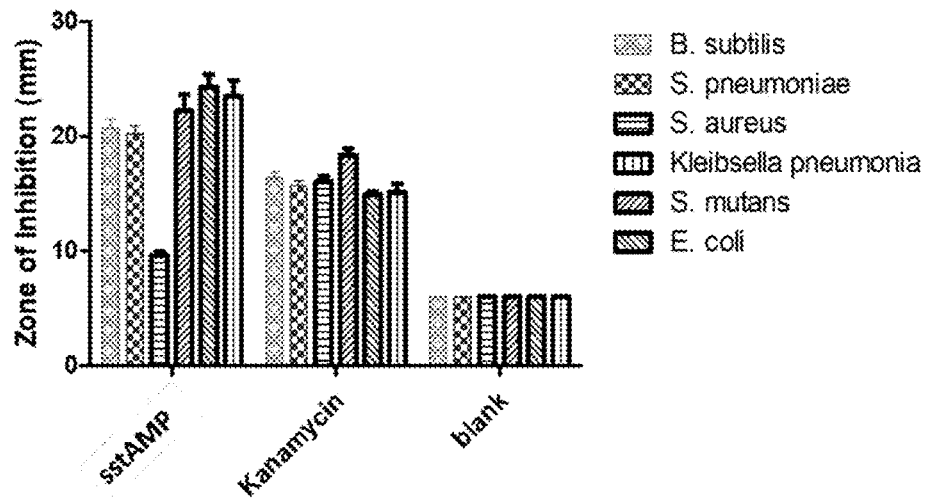
FIG. 1 is a graph depicting the zone of inhibition obtained during agar diffusion test by sstAMP as compared to kanamycin (results presented as mean±SD, n=3) (ssTAMP showed better activity in comparison to Kanamycin against all tested bacteria except *S. aureus*).

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer or a bacterial infection.

"Hydrocarbon staple" refers to a hydrocarbon chain that may be chemically bonded at each end of the chain to a different amino acid residue, effectively "stapling" or connecting the hydrocarbon chain to the amino acid sequence.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter pertains to the field of pharmaceuticals, particularly to a stapled and specifically targeted antimicrobial peptide (ssTAMP2) (SEQ ID NO: 1) and its use as an antimicrobial agent and as an anti-cancer agent. For example, ssTAMP2 can be useful as an effective antibacterial drug, as antibiofilm agents, an antibacterial coating, or as an anti-cancer drug.

According to an embodiment, ssTAMP2 can maintain a potent antibacterial activity while completely overcoming AMP toxicity. Cytotoxicity is an important consideration for determining whether medication candidates can be effective in a medical context. As described herein, ssTAMP2 toxicity was evaluated using MCF-7 and A549 tumor cells. Intriguingly, even at a concentration of 250 µg/ml, ssTAMP2 was safe and more than 50% of cells viable in both MCF-7 and A549. Accordingly, sSTAMP2 is a possible option for an anticancer medication due to its great selectivity to tumor cells.

Antimicrobial peptides (AMPs) can be an efficient substitute for traditional antibiotics, especially against antimicrobial resistant bacteria. The composition of AMPs (i.e., amino acids) allows researchers to manipulate the chemical structure of AMPs which eventually help to design efficient AMPs with enhanced pharmacokinetics, stability, activity, and toxicity profiles.

As described herein, a novel combination of stapling and specifically targeted strategies was used in a known LL-37 antimicrobial peptide to provide ssTAMP2. The ssTAMP2 demonstrated activity against *B. subtilis, S. pneumonia, S. aureus, S. mutans, E. coli* and *Kleibsella pneumonia*. In comparison to Kanamycin, ssTAMP2 showed better activity in all tested bacteria except for *S. aureus*. This indicates that the combined strategy can enhance the activity of AMPs. The ssTAMP clearly appears to be cytotoxic in MCF-7 and A549 in a concentration dependent manner. However, at lower doses the cytotoxic responses in both the cell lines are very similar, but they vary at higher doses, and MCF-7 appears to be more sensitive to ssTAMP than A549. This can be attributed to the differences in origin, metabolic processes, and growth patterns in both cell types. In both cases, ssTAMP exhibits its cytotoxic potential in cancer cell lines.

In an embodiment, the present subject matter relates to a stapled and specifically targeted antimicrobial peptide (ssTAMP2) having the sequence LPSTGEKDTAVERNGGFFRKSKEK-S5-GKE-S5-KRIV (SEQ ID NO: 1). In an embodiment, SEQ ID NO: 1 includes an amidated C-terminal valine.

The ssTAMP2 peptide includes a functional group, a linker, and a targeting group to improve the selectivity of the peptide. In an embodiment, the functional group includes a stapled α-helix of LL-37. In an embodiment, the functional group or α-helix structure in ssTAMP2 is FFRKSKEK-S5-GKE-S5-KRIV-NH2 (SEQ ID NO: 2). In an embodiment, the targeting group in ssTAMP2 is LPSTGEKDTAVERN (SEQ ID NO: 3). The GG residues in SEQ ID NO: 1 serve as a linker to connect the functional sequence to the targeting sequence.

According to an embodiment, the α-helix structure includes alpha-4-n-pentenyl alanine (S5) residues (non-naturally occurring amino acid residues) and the C-terminus is capped to increase the peptide positive charge. In an embodiment, an olefin hydrocarbon staple, e.g., a $C_{10}$ hydrocarbon staple, is stapled to the two S5 residues.

In an embodiment, the present subject matter relates to a pharmaceutical composition comprising the ssTAMP2 peptide and a pharmaceutically acceptable carrier.

In an embodiment, the present subject matter relates to a process for the synthesis of the ssTAMP2 peptide (SEQ ID NO: 1), including providing a cathelicidin antimicrobial peptide having the sequence FFRKSKEKIGKEFKRIV (SEQ ID NO: 4), replacing the isoleucine at position 9 of SEQ ID NO: 2 and the phenylalanine residue at position 13 of SEQ ID NO: 2 with alpha-4-n-pentenylalanine residues (S5); and bonding a hydrocarbon chain to the alpha-4-n-pentenylalanine (S5) residues. In an embodiment, the hydrocarbon chain bonded to the alpha-4-n-pentenylalanine (S5) residues can include a $C_{10}$ hydrocarbon staple. In an embodiment, the method can include performing ring-closure metathesis using a Grubbs reaction. In an embodiment, a hydrochloride salt can be used as a counter ion.

Further contemplated herein are pharmaceutical compositions comprising the stapled and specifically targeted antimicrobial peptide (ssTAMP2) (SEQ ID NO: 1), as well as methods of inhibiting microbial growth or treating or ameliorating microbial infections by administering the stapled and specifically targeted antimicrobial peptide (ssTAMP2) (SEQ ID NO: 1) to a patient in need thereof.

In one embodiment, the microbial infection treatable herein may be caused by *Staphylococcus aureus*, methicillin-resistant *Staphylococcus aureus* (MRSA), *Bacillus subtilis, Streptococcus pneumonia, Streptococcus mutans, Escherichia coli*, or *Kleibsella pneumonia*.

In an embodiment, the hydrocarbon staple may have the following chemical structure:

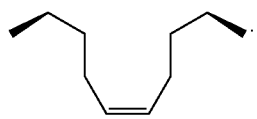

In one embodiment, the ssTAMP2 peptide (SEQ ID NO: 1) may have a molecular weight of 3,760.2 Daltons.

In one embodiment, the ssTAMP2 (SEQ ID NO: 1) may be amidated at the C-terminus, i.e. a —$NH_2$ group may be added to the carboxylic acid of the valine$^{17}$ residue. This amidation may increase the positive charge of the ssTAMP2 peptide.

In one embodiment, the present stapled peptides can be made according to the general methods taught in Phillips, C., et al. ("Design and Structure of Stapled Peptides Binding to Estrogen Receptors", J. Am. Chem. Soc. 2011, 133 (25): pp. 9696-9).

In another embodiment, the present subject matter is directed to pharmaceutical compositions comprising a therapeutically effective amount of the ssTAMP2 peptide (SEQ ID NO: 1) as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition comprising the ssTAMP2 peptide (SEQ ID NO: 1) together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present peptides are typically administered at a therapeutically or pharmaceutically effective dosage, e.g., a dosage sufficient to provide treatment for a bacterial infection. Administration of the peptide or pharmaceutical compositions thereof can be by any method that delivers the peptides systemically and/or locally. These methods include oral routes, parenteral routes, intraduodenal routes, and the like.

While human dosage levels have yet to be optimized for the present peptides, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the peptide of SEQ ID NO: 1 for treatment of a bacterial infection or cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present peptide can also be administered in sustained or controlled release dosage forms, including depot injections, osmotic pumps, pills, transdermal (including electrotransport) patches, and the like, for the prolonged administration of the peptide at a predetermined rate, preferably in unit dosage forms suitable for single administration of precise dosages.

The present peptide may also be administered in compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of ssTAMP2 (SEQ ID NO: 1), the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active peptide as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active peptide in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active peptide contained in such parenteral compositions is highly dependent on the specific nature thereof, as well as the activity of the peptide and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active peptide alone or in combination with other pharmaceutically acceptable excipients can also be administered.

Formulations of the ssTAMP2 peptide may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present peptides have valuable pharmaceutical properties, which make them commercially utilizable. Accordingly, the present subject matter relates to use of the stapled and specifically targeted antimicrobial peptide (ssTAMP2) (SEQ ID NO: 1) for the treatment of microbial infections, such as *Staphylococcus aureus*, methicillin-resistant *Staphylococcus aureus* (MRSA), *Bacillus subtilis*, *Streptococcus pneumonia*, *Streptococcus mutans*, *Escherichia coli*, or *Kleibsella pneumonia* infections.

In an embodiment, the stapled antimicrobial peptide (ssTAMP2) (SEQ ID NO: 1) can be used to inhibit a bacterial infection in a patient.

In an embodiment, the stapled antimicrobial peptide (ssTAMP2) (SEQ ID NO: 1) can be used to treat cancer in a patient. In an embodiment, the cancer can be selected from breast cancer and lung cancer.

The present subject matter further relates to a method of treating or preventing a disease comprising administering to a patient in need thereof a therapeutically effective amount of the stapled and specifically targeted antimicrobial peptide (ssTAMP2) (SEQ ID NO: 1).

In particular, the present subject matter relates to a method of treating one of the above-mentioned diseases or disorders comprising administering to a patient in need thereof a therapeutically effective amount of the stapled and specifically targeted antimicrobial peptide (ssTAMP2) (SEQ ID NO: 1).

In the above methods, the patient is preferably a mammal, more preferably a human. Furthermore, in the above methods, the ssTAMP2 peptide (SEQ ID NO: 1) can be used in combination therapy with one or more additional active agents.

The following examples relate to various methods of manufacturing certain specific peptides as described herein.

EXAMPLES

Example 1

Bacterial Strains and Culture Conditions

Microbial cultures were procured from the microbiology department, College of Pharmacy, King Saud University, Riyadh. Strains were grown aerobically at 37° C. with shaking in Muller Hilton media.

Example 2

Solid-Phase Peptide Synthesis

The ssTAMP peptide was synthesized and purified at >95% purity by CPC scientific Inc. The counter ion was HCl and not trifluoroacetate (TFA) to avoid TFA effects on antimicrobial activity.

Fmoc-based solid peptide synthesis was used to synthesize ssTAMP2 peptide (SEQ ID NO: 1) with a side-chain protection group for certain residues (Table 1). The stapling technique used in synthesizing ssTAMP2 (SEQ ID NO: 1) was the established technique published by Phillips, C. et al. ssTAMP2 (SEQ ID NO: 1) was synthesized via an i, i+4 stapling approach in which two non-natural amino acids were incorporated in the original sequence of a cathelicidin antimicrobial peptide having the sequence FFRK-SKEKIGKEFKRIV (SEQ ID NO: 4). The non-natural amino acids were alpha-4-n-pentenylalanine (S5) residues and both S5 residues replaced the isoleucine and phenylalanine residues at position 9 and 13 in the original sequence (SEQ ID NO: 4).

The ring-closure metathesis was done using a Grubbs reaction. Specifically, a 1 mg/mL solution of the first-generation Grubbs catalyst benzylidene-bis(tricyclohexylphosphino)-dichlororuthenium was added to the peptide resin and incubated for 2 hours at 50° C. temperature. Thus, Grubb metathesis, i.e., ring closure, was done by linking two non-natural amino acids of the peptide while attached to the resin. The olefin hydrocarbon was used to staple the α-helix structure while GG residues were used to connect the functional sequence (FFRKSKEK-S5-GKE-S5-KRIV-NH$_2$) (SEQ ID NO: 2) to targeting sequence (LPSTGEKD-TAVFRN) (SEQ ID NO: 3). The targeting sequence was derived from gram positive bacteria that is a motif sequence in the bacterial wall. The ssTAMP2 peptide counter ion was hydrochloride (HCl) salt. RP-HPLC was used to confirm the purity of ssTAMP2 (>95%) purity by CPC Scientific Inc. and mass spectroscopy confirmed that ssTAMP2 has a molecular weight of 3,760.2 Daltons.

ssTAMP1 was amidated at the C-terminus i.e., —NH$_2$ group was added to the carboxylic acid of the valine[17] residue. The amidation increased the positive charge of the ssTAMP1 peptide.

TABLE 1

| | Sequence | C-terminus |
|---|---|---|
| ssTAMP | $^1$LPSTGEKDTA$^{10}$VFRNGGFFRK$^{20}$SKEK$^{24}$-S5-$^{26}$GKE$^{28}$-S5-KRIV$^{33}$ (SEQ ID NO: 1) | —NH2 |
| Side chain protection groups for SEQ ID NO: 1 | Leu-Pro-Ser(tBu)-Thr-Gly-Glu(OtBu)-Lys(Boc)-Asp(OtBu)-Thr(OtBu)-Ala-Val-Phe-Arg(Pbf)-Asn-Gly-Gly-Phe-Phe-Arg(Pbf)-Lys(Boc)-Ser(tBu)-Lys(Boc)-Glu(OtBu)-Lys(Boc)-S5-Gly-Lys(Boc)-Glu(OtBu)-S5-Lys(Boc)-Arg(Pbf)-Ile-Val [(SEQ ID NO: 1) with side protection groups] | —NH2 |
| S5 | Alpha-4-n-pentenyl alanine | |

TABLE 1-continued

| Sequence | | C-terminus |
|---|---|---|
| Original sequence (LL-37) | $^1$FFRKSKEKIGKEFKRIV$^{17}$ (SEQ ID NO: 4) | No C-amidation |

Example 3

Screening of Synthesized AMPs for Antimicrobial Analysis

The agar diffusion method was used to examine the synthesized ssTAMP's antibacterial activity. Pure colonies of *Bacillus subtilis, Streptococcus pneumonia, Staphalycoccus aureus, Streptococcus mutans, Escherichia coli*, and *Kleibsella pneumonia* were used for antibacterial susceptibility testing according to Clinical Laboratory Standards Institute (CLSI) 2021 guidelines by using a modified Kirby-Bauer disk diffusion technique. In brief, homogeneous colonies were chosen from each microbial strain and grown on Mullar Hilton broth at log phase. 0.5 McFarland standard culture was used to spread on to the Mullar Hilton agar plates. Freshly prepared 30 µl each of Kanamycin 10 µg/ml and ssTAMP 100 µg/ml was poured into 6 mm diameter well, blank well with equivalent amount of saline served as a positive control. The plates were incubated for 24 hours, and the diameter of the inhibition zone was measured to determine if the findings were susceptible or resistant. The full analysis was carried out three times.

Example 4

Determination of Minimum Inhibitory Concentration (MIC)

The resazurin-based turbidometric (TB) assay was adopted to demonstrate the inhibition effects of ssTAMP against *S. aureus* and MRSA. The standard antibiotic, kanamycin, was used as positive control. Broth microdilutions were performed precisely according to the Clinical and Laboratory Standards Institute (CLSI) protocol. In a 96-well round-bottom microtiter plate, for each bacteria culture, the assay triplicate with positive control kanamycin, and negative control as no inoculum. The first well, 200 µL of 2X LB media, was mixed with 100 µg/ml ssTAMP and 2-fold serially diluted. Lastly, 100 µl was removed from the eighth well and discarded. The final concentration of antibiotics and ssTAMP was now one-half of the original concentration in each well. Similarly, kanamycin was added in the range of 10 µg/ml to 0.15625 µg/ml. Then, 5 µl of diluted bacterial suspension ($1.5 \times 10^6$ cell/ml) was added into all wells except negative control wells and mixed thoroughly. Microdilution was performed in triplicate for each bacterial species. After an overnight incubation at 37° C., growth was observed and recorded. The lowest concentration prior to colour change was considered as the Minimum Inhibitory Concentration (MIC).

Example 5

Cytotoxicity & MTT Testing

MCF-7 and A549 cells were cultured under aseptic conditions at 37° C. and 5% $CO_2$ using Dulbecco's Modified Eagle's Medium (DMEM), accompanied with 1% mixture of "Penicillin-Streptomycin", and 10% Fetal Bovine Serum (FBS). The cells were processed and grown in a sterile environment and all the procedures were done in a biosafety cabinet. The cells were harvested using 0.25% trypsin containing EDTA and phenol red, once they reached around 80% confluency. To test the in-vitro toxicity of the antimicrobial peptide, the harvested cells were seeded in 96 well plates for conducting a cell viability assay using MTT (3-(4,5-dimethylthiazol-2-yl)-2,5-diphenyl tetrazolium bromide).

In order to investigate the in-vitro cytotoxicity of ssTAMP using the MTT assay, cell viability was carried out in MCF-7 and A549 cells. To achieve a cell density of $5 \times 10^5$ cells/mL, trypsin was introduced to the cells during their exponential phase of growth. After that, 100 µL of media and the cell suspension (15000 cells/well) were placed on a flat-bottomed microplate, where they were left to attach to the bottom overnight. The following day, 10 µL of freshly prepared medium containing ssTAMP concentrations ranging from 7.81 to 1000 g/mL was added to the preexisting medium. As a negative control, a triplicate of untreated, FBS-free DMEM were used. Each product's dilution was tested three times. After 24 hours, the media was carefully removed from the wells. After that, 10 µL of MTT solution (5 mg/mL in PBS) and 90 µL of the medium were added. After that, this combination was incubated for 4 hours at room temperature. The medium and MTT in the culture fluid were then drawn out, leaving the formazan crystal precipitate. Formazan was dissolved for 15 minutes at room temperature in a 100 mL DMSO. At 570 nm, the absorbance was measured (Synergy HT, BioTek Inst., VT, USA). Cell viability was calculated as a percentage of the absorbance when compared with negative control considered as 100%. The cytotoxic effects of ssTAMP on MCF-7 and A549 cells were expressed as $IC_{50}$ values.

Example 6

Zone of Inhibition

The agar diffusion method was used to test antimicrobial susceptibility of sSTAMP against *B. Subtilis, S. Pneumoniae, S. Aureus, S. Mutans, E. Coli*, and *Kleibsella pneumonia* strains (FIG. 1). Antimicrobial assessment showed a significantly high zone of inhibition for ssTAMP for the selected bacterial strains. Gram-positive bacteria, *B. subtillis, S. pneumoniae*, and *Staphylococcus aureus* and *S. mutans* showed susceptibility towards ssTAMP with zone of inhibition (ZOI) of 20.63±0.85, 20.17±0.72, 9.60±0.32, and 22.23±1.39 compared to the kanamycin ZOI 16.40±0.46, 15.70±0.4, 16.07±0.45, and 18.37±0.58, respectively ($p \leq 0.05$). Gram-negaive bacteria *E. coli* and *K. pneumonia* showed susceptibility towards ssTAMP with ZOI 24.30±1.08 and 23.47±1.40 compared to the kanamycin ZOI 14.90±0.25, 15.10±0.74, respectively (Table 2).

TABLE 2

ZOI and MIC for each tested microorganism for ssTAMP vs. Kanamcyin

| Organism name | Zone of inhibition (mm) ssTAMP | Zone of inhibition (mm) Kanamycin | Minimum Inhibitory concentration (µg/mL) ssTAMP | Minimum Inhibitory concentration (µg/mL) Kanamycin |
|---|---|---|---|---|
| B. subtilis | 20.63 ± 0.85 | 16.40 ± 0.46 | 8.33 ± 2.08 | 1.67 ± 0.42 |
| S. pneumonia | 20.17 ± 0.72 | 15.70 ± 0.4 | 10.42 ± 2.08 | 1.67 ± 0.42 |
| S. aureus | 9.60 ± 0.32 | 16.07 ± 0.45 | 12.50 ± 0.000 | 1.67 ± 0.42 |
| S. mutans | 22.23 ± 1.39 | 18.37 ± 0.58 | 8.33 ± 2.08 | 1.04 ± 0.21 |
| E. coli | 24.300 ± 1.08 | 14.90 ± 0.25 | 5.21 ± 1.05 | 1.46 ± 0.55 |
| Kleibsella pneumonia | 23.47 ± 1.40 | 15.10 ± 0.74 | 5.21 ± 1.042 | 1.25 ± 0.00 |

Figure 2:
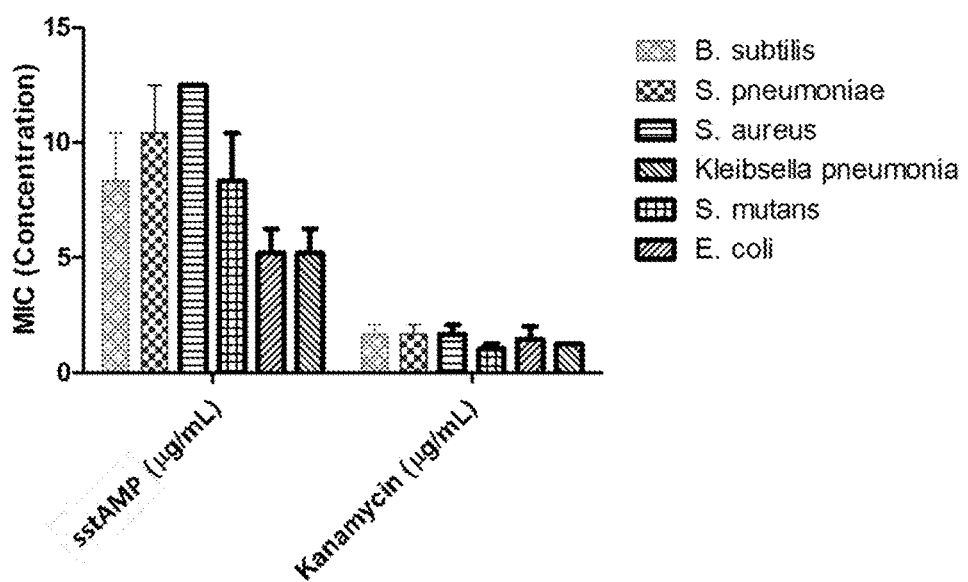
FIG. 2 is a graph depicting minimum inhibitory concentration calculated by the microdilution method showing the activity against the selected bacteria *B. subtilis, S. pneumonia, S. aureus, S. mutans, E. coli* and *Kleibsella pneumonia* (results presented as mean±SD, n=3).

Moreover, the minimum inhibitory concentration (MIC) calculated by the microdilution method showed the activity against the selected bacteria B. subtilis, S. pneumonia, S. aureus, S. mutans, E. coli and Kleibsella pneumonia were 8.33±2.08, 10.42±2.08, 12.50±0.000, 8.33±2.08, 5.21±1.05 and 5.21±1.042 in comparison to kanamycine 1.67±0.42, 1.67±0.42, 1.67±0.42, 1.04±0.21, 1.46±0.55, and 1.25±0.00, respectively (FIG. 2A-2B, Table 2).

Example 7

Cytotoxicity

Figure 3A:
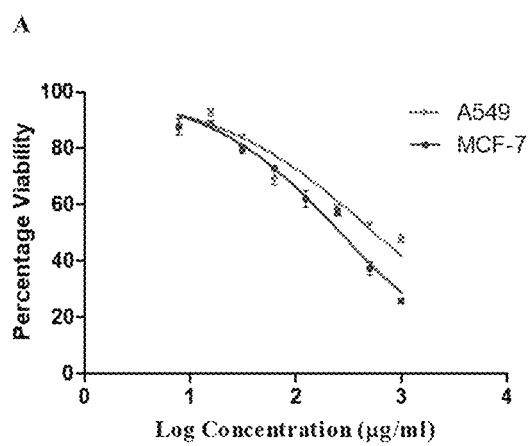
FIGS. 3A-3B are graphs of cytotoxicity after 24 h of incubation with ssTAMP (3A) MCF-7 cells and (3B) A549 cells with $IC_{50}$ values (µg/mL).
Figure 3B:
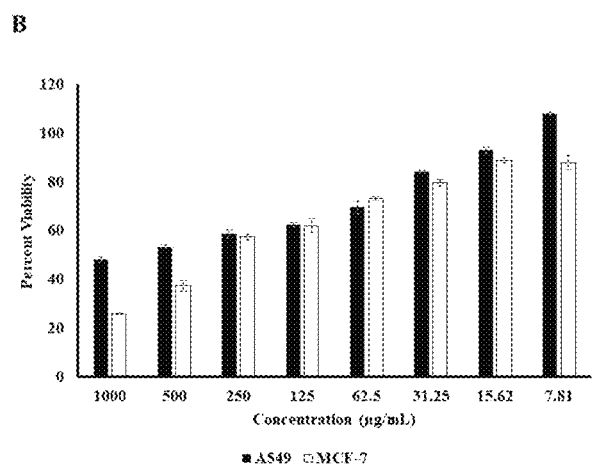

The percentage cell viabilities of MCF-7 breast cancer cells and A549 lung cancer cells against varying concentrations of ssTAMP are presented in FIGS. 3A-3B. Cell proliferation of ssTAMP was examined at 7.81-1000 µg/mL, where the observed $IC_{50}$ were 558.2 and 265.0 µg/mL at 24 h against MCF-7 and A549 cells, respectively (Table 3). The MTT assay results demonstrate a concentration-dependent anti-cell proliferation of ssTAMP against MCF-7 and A549. The cytotoxicity starts to appear at the lowest concentration of ssTAMP used (7.81 µg/mL in MCF-7, and 15.62 µg/mL in A549). The effect pattern of the ssTAMP in both the cell lines is similar up to the concentration of 250 µg/mL. However MCF-7 appear to be more sensitive at higher concentrations of ssTAMP above 250 µg/mL.

TABLE 3

$IC_{50}$ values (µg/mL) of ssTAMP in MCF-7 and A549 cells.

| | Cytotoxicity by MTT Assay | |
|---|---|---|
| Cells | MCF-7 | A549 |
| $IC_{50}$ (µg/ml) | 558.2 | 265.0 |
| R2 | 0.8454 | 0.9658 |

It is to be understood that the stapled and specifically targeted antimicrobial peptide is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A stapled and specifically targeted antimicrobial protein comprising an amino acid having the sequence LPST-GEKDTAVERNGGFFRKSKEK-S5-GKE-S5-KRIV (SEQ ID NO: 1 and a hydrocarbon staple bound to the two S5 residues of SEQ ID NO: 1, wherein the two S5 residues comprise alpha-4-n-pentenylalanine amino acid residues.

2. The stapled antimicrobial protein of claim 1, wherein the hydrocarbon staple is a $C_{10}$ hydrocarbon staple.

3. The stapled antimicrobial protein of claim 1, wherein the terminal valine is an amidated C-terminal valine.

4. A pharmaceutical composition comprising the stapled and specifically targeted antimicrobial peptide of claim 1 and a pharmaceutically acceptable carrier.

5. A method of inhibiting bacterial growth in a subject, comprising administering the pharmaceutical composition of claim 4 to a subject in need thereof:
   wherein the bacterial growth comprises growth of bacteria selected from the group consisting of *Staphylococcus aureus, Bacillus subtilis, Streptococcus pneumonia, Streptococcus mutans, Escherichia coli*, and *Kleibsella pneumonia*.

6. A method of inhibiting the growth of breast cancer cells or lung cancer cells in a subject, comprising administering the pharmaceutical composition of claim 4 to a subject in need thereof.

7. The method of claim 6, wherein the growth of cancer cells comprises growth of breast cancer cells.

8. The method of claim 6, wherein the growth of cancer cells comprises the growth of lung cancer cells.

* * * * *